United States Patent [19]

Bakel

[11] Patent Number: 4,507,250
[45] Date of Patent: Mar. 26, 1985

[54] PROCESS FOR PRODUCING N-PHOSPHONOMETHYLGLYCINE ACID

[75] Inventor: Izhak Bakel, Ramat Gan, Israel

[73] Assignee: Geshuri Laboratories Ltd., Tel Mond, Israel

[21] Appl. No.: 609,213

[22] Filed: May 11, 1984

Related U.S. Application Data

[63] Continuation-in-part of Ser. No. 521,072, Aug. 8, 1983, abandoned.

[30] Foreign Application Priority Data

May 17, 1983 [IL] Israel .................................. 68716

[51] Int. Cl.$^3$ ............................................. C07F 9/38
[52] U.S. Cl. ............................. 260/502.5 F; 260/501.12
[58] Field of Search .............................. 260/502.5 F

[56] References Cited

U.S. PATENT DOCUMENTS

| | | | |
|---|---|---|---|
| 3,907,652 | 9/1975 | Wagenknecht et al. | 260/502.5 F |
| 3,950,402 | 4/1976 | Franz | 260/502.5 F |
| 3,954,848 | 5/1976 | Franz | 260/502.5 F |
| 3,969,398 | 7/1976 | Hershman | 260/502.5 F |
| 4,147,719 | 4/1979 | Franz | 260/502.5 F |

FOREIGN PATENT DOCUMENTS 2049697 12/1980 United Kingdom ......... 260/502.5 F Primary Examiner—J. E. Evans
Attorney, Agent, or Firm—Cushman, Darby & Cushman

[57] ABSTRACT

The invention provides a process for producing N-phosphonomethylglycine acid (NPMG) comprising (a) oxidizing an N-(phosphonomethyl) iminodiacetic acid (NPMIDA) derivative of the general formula I

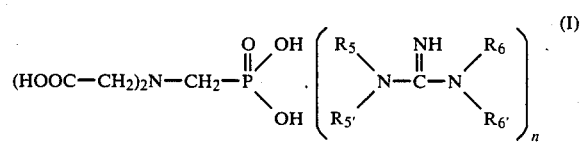

wherein n is 1 or 2 and $R_5$, $R_{5'}$, $R_6$ and $R_{6'}$ are independently H, $NH_2$,

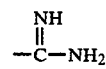

or an aryl, cycloalkyl or straight or branched chain alkyl or alkenyl group optionally substituted by hydroxy or halogen, or an alkylaryl group, provided that at least one of $R_5$, $R_{5'}$, $R_6$ or $R_{6'}$ is hydrogen, to produce a corresponding iminourea salt of NPMG and then (b) reacting the salt with an acid stronger than NPMG whereby NPMG is produced and there remains in solution the iminourea salt of the stronger acid.

12 Claims, No Drawings

PROCESS FOR PRODUCING N-PHOSPHONOMETHYLGLYCINE ACID

This application is a continuation-in-part of patent application Ser. No. 521,072 filed Aug. 8, 1983 and entitled Process for Producing N-Phosphonomethylglycine Acid, now abandoned.

The present invention relates to a method of producing N-Phosphonomethylglycine acid (NPMG).

More particularly, the invention is concerned with an improved and economical process for the preparation of NPMG by the oxidation of N-(Phosphonomethyl)iminodiacetic acid (NPMIDA) iminourea salts with oxygen or an oxygen containing gas in the presence of a catalyst.

The compound NPMG is known for more than twenty years and it can be prepared as mentioned in U.S. Pat. No. 3,160,632 (1961) by the oxidation of the corresponding aminophosphinic compounds utilizing mercuric chloride and other oxidizing agents.

Certain NPMG salts are known and widely used as broad spectrum herbicides having little or no residual effect.

NPMG in itself is a very effective phytotoxicant or herbicide, however, because it is relatively insoluble in water and conventional organic solvents, it is not as readily amenable to commercial formulation as are its derivatives. It is therefore generally preferred to utilize the more readily soluble derivatives of this compound in which at least one of the hydrogens in the hydroxy groups of NPMG has been replaced to form a water soluble salt.

NPMG is most often prepared by the oxidation of NPMIDA. This NPMG can be produced by oxidation of NPMIDA using concentrated $H_2SO_4$ (Israeli Pat. No. 41842), $H_2O_2$ with concentrated $H_2SO_4$ (Israeli Pat. No. 42393) and electrolytic oxidation (U.S. Pat. No. 3,859,183).

Oxidation of NPMIDA may also be carried out with oxygen or oxygen containing gas in the presence of a catalyst (U.S. Pat. No. 3,969,398). The advantages of the catalytical oxidation over the known methods mentioned above is that it does not require expensive chemicals or special equipment and it is very easy to recover the NPMG in pure state. Severe drawbacks of this method, however, come from the fact that NPMIDA, used as starting material, is poorly soluble in water ($N \approx 4\%$ at 100° C.). As a consequence of the low solubility of NPMIDA, aqueous solutions have to be employed in a large amount thereby reducing the useful capacity of the reactor and thus increasing the energy required.

In order to eliminate the above disadvantages a method is disclosed in U.S. Pat. No. 4,147,719 according to which the NPMIDA amine salts are used as starting material. From the point of view of energy saving, only those salts whose solubility is close to the upper limit of the saturated concentration may be used in large scale practice. Thus, the most widely used salt is the isopropylamine salt of NPMIDA.

Data disclosed in U.S. Pat. No. 4,147,719 show that during the oxidation of the NPMIDA salts a considerable amount of by-products are formed (such as N-Methyl-N-Phosphonomethylglycine and Methylaminomethylphosphonic acid), which reduces the yield of the end product since said by-products are difficult to remove from the desired product.

Although the formation of by-products may be reduced if the conventionally used charcoal catalysts are replaced by an expensive platinum catalyst there are still several disadvantages:

A. the use of expensive platinum catalyst in the oxidation step may need a complicated regeneration procedure for reuse.

B. Although said U.S. patent claims that said platinum on carbon catalyst provides concurrent oxidation of the formaldehyde coproduct (probably via formic acid) as it is formed, data disclosed in the above patent show that there is still high concentration of formaldehyde (up to 30% of the theoretical amount in some cases) that remained unoxidized. This coproduct is very difficult to remove before directly using the said salt solution as herbicide.

C. It is believed that the above by-products (N-Methyl N-Phosphonomethylglycine and Methylaminomethylphosphonic acid) resulted from reductive methylation known in the art as Leuckart reaction or the closely related Eschweiler-Clarke methylation (organic reaction Vol V, page 307, John Wiley & Sons, 1949, New York) in which primary or secondary amine (as well as aminoacid) is heated with formaldehyde or preferably with formaldehyde and formic acid yielding methylated amine derivatives in good yield according to the reaction:

$$RNH_2 + 2CH_2O + 2HCOOH \xrightarrow{\Delta} RN(CH_3)_2 + 2CO_2 + 2H_2O$$

Therefore, the oxidation of an NPMG salt of primary or secondary amine may also yield methylated amines as co-products thus resulting in a mixture of NPMG amines salts instead of one sole product. Although said patent (U.S. Pat. No. 4,147,719) has found that using Pt/c as catalyst in the above oxidation can minimize or partly eliminate said phosphonic acid by-product, nothing is said about the possibility of obtaining methylated amine by-products resulting from the said Leuckart reaction. Moreover, U.S. Pat. No. 4,147,719 does not describe the carrying out of any analysis of the amine cations of the NPMG salts obtained by the said oxidation.

D. Isopropylamine salt of NPMG is obtained in the most favourable case in the form of about 20% aqueous solution, thus a large amount of water still has to be removed from the solution (about 50%) if the product is formulated in the commercially available form of a 36% aqueous solution.

E. The amines of NPMIDA salt (including isopropylamine) may undergo dealkylation followed by oxidation to carbonyl or carboxylic acid derivatives when subjected to an oxidation utilizing oxygen over said platinum catalyst.

Therefore, the NPMG amine salts according to U.S. Pat. No. 4,147,719 will contain oxidation degradation and methylation products of the amine, formaldehyde and methylated phosphonic acid derivatives. The above by-products are difficult to separate from the desired product and therefore the oxidation solution cannot be used directly as a herbicide.

It has now been surprisingly discovered in an improved process for producing NPMG acid that iminoureas can serve both as salt forming cation and formaldehyde coproduct scavenger during the oxidation of NPMIDA with molecular oxygen over activated carbon and thus the disdvantageous features of the prior art can be minimized or eliminated. Furthermore, optionally adding various amounts of iminourea-strong acid salts to the above NPMIDA-iminourea salt solution increase further the binding of formaldehyde corproduct. Moreover, after separation of NPMG by heating with hydrochloric acid the resulting iminourea salts can be reused which makes the process feasible and practical.

In according to the present invention, there is now provided a process for producing N-phosphonomethylglycine acid (NPMG) comprising (a) oxidizing an N-(phosphonomethyl) iminodiacetic acid (NPMIDA) derivative of the general formula I

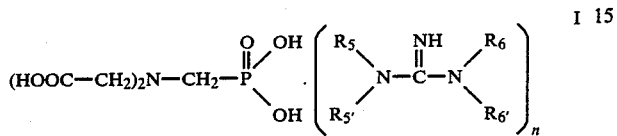

wherein n is 1 or 2 and $R_5$, $R_{5'}$, $R_6$ and $R_{6'}$ are independently H, $NH_2$,

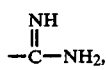

or an aryl, cycloalkyl or straight or branched chain alkyl or alkenyl group optionally substituted by hydroxy or halogen, or an alkylaryl group, provided that at least one of $R_5$, $R_{5'}$, $R_6$ or $R_{6'}$ is hydrogen, to produce a corresponding iminourea salt of NPMG, optionally adding iminourea-strong acid salts and then (b) reacting said salt with an acid stronger than NPMG whereby NPMG is produced and there remains in solution the iminourea salt of said stronger acid.

In the preferred commercial embodiment of the present invention said process includes the further recycling step of (c) reacting said resulting iminourea salts of said stronger acid with an NPMIDA alkali metal salt to produce a salt of formula I for use in process step (a).

Preferably said alkali metal is selected from the group consisting of sodium and potassium with sodium being especially preferred.

As will be realized said strong acid can be an organic acid such as sulfonic acid or an inorganic acid such as hydrochloric or sulfuric acid with hydrochloric acid being especially preferred. The iminourea-strong acid salts are those produced from the above-defined iminourea (a) and the above strong acid such as iminourea hydrochloride or sulphate. However, the iminourea can be the same or different from the one employed in the NPMIDA salt.

Furthermore said aryl group is preferably phenyl optionally substituted by one or more halogen or alkyl groups.

In unpublished copending Israel specifications 65187, 66137 and 66824, there are described processes for producing N-phosphonomethylglycine amine and iminourea salts using certain iminourea salts of NPMIDA as a starting material, however said specifications were not directed to the production of pure NPMG acid in a simple inexpensive and commercial process so that desired salts could be produced in pure state directly from the pure acid and in fact do not teach or suggest the now discovered fact that in order to get a pure salt of NPMG it is worthwhile to produce pure free NPMG acid in aqueous solution, to separate the acid, whereby most of the above mentioned by-products remain in the mother liquid and then to react the pure acid with the appropriate base to form the desired salt.

Furthermore the preferred commercially important recycling step c as described herein is neither taught nor suggested in any of said prior specifications or patents.

In essence the present invention provides a process which involves:

(I) Reacting NPMIDA with iminourea in aqueous solution to produce an NPMIDA iminourea salt of formula I, optionally adding iminourea HCl;

(II) Contacting said NPMIDA iminourea salt with an oxygen containing gas preferably in the presence of catalyst to form a mixture of NPMG salts of iminourea and iminourea formaldehyde condensation products;

(III) Reacting the above derivatives of NPMG with an acid such as hydrochloric acid to regenerate the iminourea as the stronger acid (e.g., hydrochloric) salt and forming the water insoluble NPMG; and (IV) Reacting the above iminourea-hydrochloride salts with an alkali metal salt of NPMIDA to reproduce the NPMIDA-Inimourea salt of formula I, which salt is separated after saturation with a salt, e.g. sodium chloride, calcium chloride, postassium chloride, ammonium chloride etc. and sent back to the oxidation step (II).

It is believed that the process takes place in accordance with the following equations:

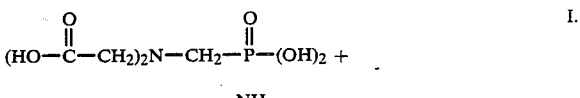

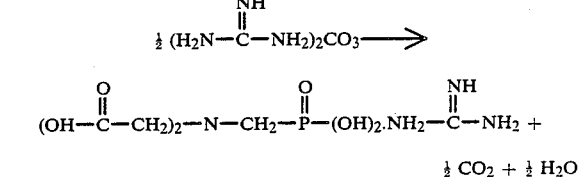

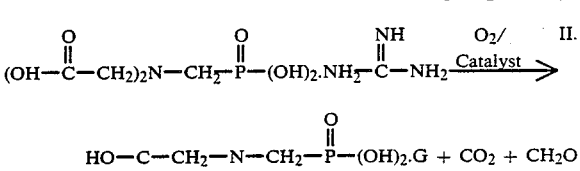

G = Guanidine and Guanidine - Formaldehyde condensation products

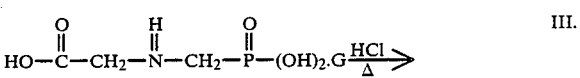

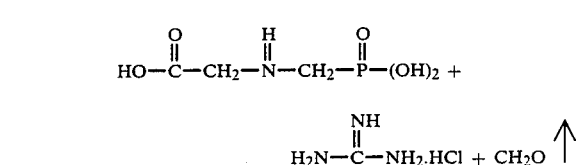

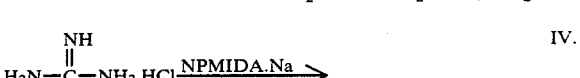

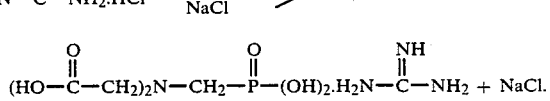

As indicated, a major problem in the prior art processes for preparing NPMG acid is the presence of formaldehyde which is a coproduct in the oxidation process. It is known that Guanidyl groups bind formaldehyde at elevated temperature in neutral or acid solution. Simple substituted guanidine salts, bind up to 2 moles for each guanidine group; free guanidine salts up to 3 moles of formaldehyde. It was also found that formaldehyde can form cross-linking methylene bridges between amino groups of amino acid on the one hand and guanidyl groups on the other hand (H. F. Conrat and H. S. Olcott J. Amer. Chem. Soc., 68 34–37 (1946) and 70 2674 (1948)) according to the reaction:

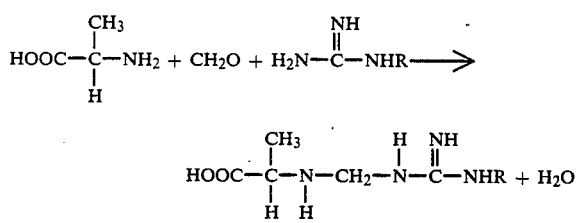

On the other hand said Leukart reductive methylation fails with a compound such as iminourea, thus no irreversible reductive methylation of iminourea takes place (Organic Reactions Vol. V page 318 John Wiley & Sons 1949 N.Y.).

Therefore all the possible compounds of iminourea and formaldehyde are loose ones and heating these compounds with dilute solution of strong acid will easily liberate the free iminourea.

Based on the above information it is believed that in the above oxidation of NPMIDA Iminourea salt, with or without iminourea strong acid salts, (step II) the guanidyl group binds the formaldehyde coproduct either as a hydroxy methyl group or as a cross linking methylene bridge, forming the following possible mixture of NPMG salts:

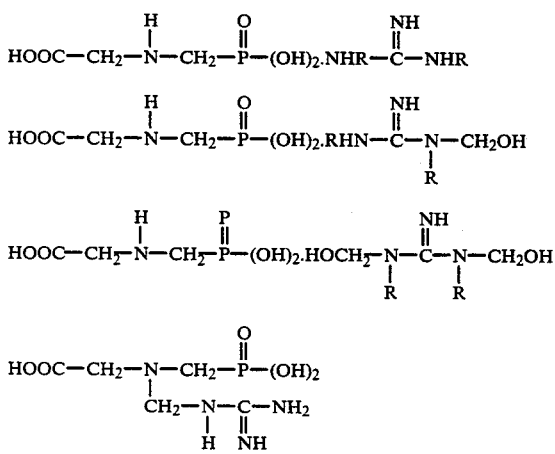

As indicated the presence of formaldehyde coproduct during the oxidation reaction contributes to and accelerates the formation of the products such as N-Methyl N-Phosphonomethyl glycine and Methylaminomethylphosphonic acid. In accordance with the present invention it has surprisingly been found that the disadvantage features of the prior art can be minimized or eliminated by the oxidation of NPMIDA Iminourea salt using activated carbon catalyst in contradistinction to the above mentioned prior art process, which uses a platinum on activated carbon catalyst.

It should be emphasised that in the above combined process (I–IV) the oxidation of NPMIDA iminourea salt (Step II) was also carried out with the mentioned platinium on activated carbon catalyst resulting in very pure salts which contains very low content of phosphonic acid and formaldehyde by-products. Thus on the one hand the time and expense required to remove formaldehyde co-product in step III can be reduced and on the other hand pure NPMG product is obtained using said platinium catalyst system in the process of the present invention.

In general, formaldehyde that is combined with a guanidyl group in the form of hydroxymethyl or as methylene derivative can be liberated by heating with dilute solution of strong acid, therefore in step III the above NPMG salt solution of Iminourea-Formaldehyde condensation products are heated with at least an equivalent amount of 20% hydrochloric acid during which the formaldehyde is distilled out and the iminourea is liberated. The solution is subjected to evaporation under reduced pressure at 60° C. to obtain a concentrated solution (25% NPMG in water). After cooling the solution to about 10° C. the NPMG is precipitated as a white solid. The slurry is filtered and the filtrate contains the iminourea-hydrochloride salt which is taken for reuse.

In step IV, the above Iminourea-Hydrochloride salt is slowly added to an aqueous solution of NPMIDA solution salt (produced by neutralization of aqueous slurry of NPMIDA with equivalent amount of an alkali base such as Sodium Hydroxide). After stirring for ½ hour and adding Sodium Chloride to saturate the aqueous solution, the insoluble NPMIDA salt is filtered and sent back to the oxidation stage in II.

The iminourea of the above salts are those prepared from low molecular weight iminourea i.e. having a molecular weight about 500 such as: Guanidine, 1-amino guanidine, N,N'-diamino guanidine, biguanide, methyl guanidine, dimethyl guanidine, trimethylguanidine, ethyl guanidine, diethyl guanidine, triethyl guanidine, phenyl guanidine, O-tolyl guanidine, N,N'-diphenyl guanidine, N,N'-di-o-tolyl guanidine, N,N'-di-P-tolyl guanidine, N,N',-di-4-ethyl phenyl guanidine, N,N'-di-4-chlorophenyl guanidine, N,N'-di-4-bromo phenyl guanidine, N,N'-ethylene diguanidine, N,N'-propylene diguanidine, N,N'-butylene diguanidine and the like.

Preferably the iminourea of said salt of formula I is selected from the group consisting of guanidine, aminoguanidine, diphenylguanidine and di-o-tolyl guanidine and aminoguanidine is especially preferred.

In conducting the oxidation processes the temperature of reaction can be from as low as 20° C. to 125° C. or even higher. It is preferred, for ease of reaction and to obtain the best yield of product, to conduct said process at from about 70° C. to about 120° C.

The time of reaction is not narrowly critical and can vary from 15 minutes heating time to as high as 40 or more hours. Of course, it is obvious to those skilled in the art that the yield of the product will vary with the reaction time and the temperature of the reaction.

The process is carried out in an aqueous media. It is preferred to employ a saturated solution of N-(Phosphonomethyl)iminodiacetic salt in water. However, for ease of operation, the process is also operable at lower or higher concentration in water.

The ratio of reactants, that is the oxidizing agent and the N-(phosphonomethyl)iminodiacetic acid (NPMIDA) salt is not narrow. For best yields one should employ at least a stoichiometric amount of oxidizing agent, e.g. ½ mole of $O_2$ for each equivalent of N-(Phosphonomethyl) iminodiacetic salt. In actual practice, however, to obtain the best yields, one employs ½ to 1 mole of oxygen for each mole NPMIDA salts. When a free oxygen-containing gas is employed it is preferred for convenience to conduct the process of this invention at a total pressure of from 0.5 kg/cm² to 200 kg/cm². It is even more preferred to conduct said process at pressure of from 1 kg/cm² to 5 kg/cm².

The manner in which the oxidation takes place, e.g., the manner in which the aqueous solution of the iminodiacetic acid salts (NPMIDA) is contacted with the molecular oxygen containing gas and catalyst (activated carbon or metal catalyst) can vary greatly. For example the Iminodiacetic acid salt solution can be placed in a closed container with some free space containing molecular oxygen and shaken vigorously or agitated by stirring or molecular oxygen containing gas can be bubbled through a straight tube or a tube with a fritted diffuser attached thereto. The contacting can also be accomplished in a tubular continuous reactor packed with activated carbon.

The oxidizing agent which can be employed to prepare the compounds of the present invention include oxygen, air, oxygen diluted with helium, argon, nitrogen or other inert gas in the presence of catalysts such as:

activated carbon, metallic catalysts (pt, Pd, Rh, Ru, etc.) alone or on activated supports such as activated charcoal, aluminium oxide, asbestos etc.

The activated carbon catalysts employed are characterized by high adsorptive capacity for gases, vapors and colloidal solids and relatively high specific surface areas. The specific surface area of the activated carbon can be from 100-2000 square meters per gram. It is preferred to employ activated carbons having a specific surface area of 400 to 1600 square meters per gram.

The activated carbons employed in said process can be in the form of powders or granules. In the powder form the activated carbons consist largely of material having a particle size finer than 325 mesh although some larger particles may also be present in the granular form. The particle size range can vary considerably, particle size of 4×10 mesh, 8×30 mesh and 20×30 mesh can be used.

The amount of granular or powdered activated carbon employed in this process can range from 0.5 to 100 or more parts by weight for every 100 parts by weight of NPMIDA salt employed.

As will be realized, the form of the activated carbon, its PH and its area, all effect the rate of the reaction of the NPMIDA salts with oxygen in this process. Experiments indicate that the reaction rate is faster when the active carbon was washed with concentrated hydrochloric acid and then washed with water (up to pH=7) before use.

Some examples of activated carbon are: Norit $p^N$-3, Norit A, Norit ACX (Amer.Norit Co., Inc., Jacksonville, Fla.), Darco 6-60 (ICI-America), grade 235 and 256 (Witco Chemical Corp), Columbia SXAC (Union Carbide) and the like.

The metal on support catalyst are the commercial 5% metal on activated carbon such as 5% Pd/c, 5% Rh/c, 5% Pt/c, 5% Pt/$Al_2O_3$ and 5% Rh/$Al_2O_3$.

While the invention will now be described in connection with certain preferred embodiments in the following examples so that it may be more fully understood and appreciated, it will be understood that it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars described are by way of example and for purposes of illustrative discussion of preferred embodiments of the present invention only and are presented in the cause of providing what is believed to be the most useful and readily understood description of procedures as well as of the principles and conceptual aspects of the invention.

In the examples, all parts, percentages and properties are by weight unless otherwise indicated.

EXAMPLE 1

A series of runs were made to oxidize NPMIDA-iminourea salt using oxygen as oxidant.

(A) This series was carried out in an acid fast 2000 ml cylindrical steel tank equipped with a heating jaket, thermometer, stirrer and air-introducing and air-outlet valve.

In each run, measured amounts of the NPMIDA and the iminourea were added to 400 ml of hot water in the reactor. The catalyst was added and the reaction mixture was heated to a temperature of 90°-95° C. The reactor was pressurized and depressurized several times with oxygen at 1-3 kg/cm² to remove the air, repressurized to the desired pressure and the solution was stirred during the reaction period. Reaction pressure was carefully monitored, and every ½ hour the reactor was bled to zero guage pressure and then repressurized to the original starting level. The course of the reaction was followed by periodic filtration of a small volume of the reaction mixture, acidification of the resultant clear solution with an equivalent amount of HCl separation the NPMG acid, and determination of the proton NMR spectrum.

In the following tabulation of test results, the "mole % NPMG" in the product is based on said NMR analysis and indicates the degree of completion of the reaction in the specified time. Where % yield is given, this indicates the amount of NPMG isolated from the solution. The activated carbon catalyst and the nobel metal catalysts employed are all commercial products.

TABLE 1

| Run | NPMIDA (g) | IMINOUREA (g) | CATALYST (g) | Pressure | Reaction time (h) | Mole % NPMG | Yield (%) NPMG | by-product* |
|---|---|---|---|---|---|---|---|---|
| 1 | 37.0 | G (15.0) | NORIT A (3.0) | 1 | 10 | 98 | 82 | Clean NMR |
| 2 | 37.0 | G (15.0) | NORIT PN-3-(3.5) | 2.1 | 2.5 | 100 | 81 | " |
| 3 | 45.0 | G (18.0) | NORIT A (4.0) | 2.0 | 2.5 | 97 | 79 | I-Trace |
| 4 | 45.0 | G (18.0) | NORIT PN-3 (3.5) | 3.0 | 1.75 | 98 | 78 | " |
| 5 | 37.0 | DPG (34.5) | NORIT PN-3 (3.0) | 1 | 10 | 100 | 80 | clean NMR |

TABLE 1-continued

| Run | NPMIDA (g) | IMINOUREA (g) | CATALYST (g) | Pressure | Reaction time (h) | Mole % NPMG | Yield (%) NPMG | by-product* |
|---|---|---|---|---|---|---|---|---|
| 6  | 37.0 | DPG (34.5) | 5% Pt/C (3.0)   | 2   | 2   | 98  | 88 | " |
| 7  | 37.0 | DTG (39.0) | NORIT A (3.0)   | 1   | 11  | 98  | 81 | clean NMR |
| 8  | 45.0 | DTG (48.0) | 5% Pt/c (3.5)   | 2.1 | 2   | 90  | 78 | I-trace |
| 9  | 37.0 | AG (22.0)  | NORIT ACX (3.0) | 1   | 12  | 98  | 88 | I-clean NMR |
| 10 | 45.0 | AG (27.0)  | 5% Pt/C (4.0)   | 2.0 | 2   | 98  | 90 | " |
| 11 | 60.0 | AG (36.0)  | NORIT PN-3 (5.0)| 3.0 | 3.0 | 95  | 86 | small amount |
| 12 | 80.0 | AG (48.0)  | NORIT PN-3 (7.0)| 2.5 | 4   | 98  | 85 | I-1% |
| 13 | 37.0 | G (18.0)   | NORIT PN-3 (3.5)| 1   | 10  | 95  | 80 | small amount |
| 14.| 37.0 | G (18.0)   | 5% Pt/C (3.5)   | 1   | 10  | 100 | 88 | " |
| 15.| 46.0 | G (36.0)   | NORIT PN-3 (4.0)| 2   | 2.5 | 95  | 60 | " |
| 16 | 45.0 | G (36.0)   | NORIT PN-3 (4.0)| 3   | 2.5 | 95  | 65 | " |

G — Guanidine Carbonate
AG — aminoguanidine Bicarbonate
DPG — Diphenyl Guanidine
DTG — DI—O—Tolyl Guanidine
I — N—Methyl-N—Phosphonomethylglycine.
*No Methylaminomethyl phosphonic acid coproduct is found.

(B) This series was carried out under the same condition as in A except the following:
1. Iminourea-strong acid salt was added to the solution of the NPMIDA-Iminourea salt before starting the oxidation.
2. The pressure of oxygen was 2.4–2.5 atmosphere The results are summarized in Table II

TABLE II

| Run | NPMIDA (g) | IMINOURA (g) | IMINOURA SALT (G) | CATALYST (g) | Reaction time (h) | Mole % NPMG | Yield % NPMG | By-Product* |
|---|---|---|---|---|---|---|---|---|
| 1 | 37.0 | G (15.0)  | G.HCl (15.3)  | NORIT A (3.0)     | 2.1 | 98  | 86 | I-small amount |
| 2 | 45.0 | G (18.0)  | GHCl (19.1)   | NORIT PN-3 (3.5)  | 2.5 | 97  | 85 | " |
| 3 | 45.0 | G (18.0)  | AG.HCl (22)   | NORIT SA-3 (3.5)  | 3.5 | 100 | 87 | I-clean NMR |
| 4 | 37.0 | G (15.0)  | AG.HCl (17.5) | NORIT A (3.0)     | 2.0 | 100 | 89 | " |
| 5 | 45.0 | AG (27.0) | G.HCl (19.1)  | NORIT SX-16 (3.5) | 2.0 | 98  | 91 | " |
| 6 | 60.0 | AG (36.0) | G.HCl (25.2)  | NORIT ACX (5.0)   | 3.0 | 97  | 88 | I-small amount |
| 7 | 60.0 | AG (36.0) | AG.HCl (28.9) | NORIT SA-3 (5.0)  | 3.0 | 100 | 87 | " |
| 8 | 80.0 | AG (48)   | AG.HCl (38.6) | NORIT PN-3 (7.0)  | 3.0 | 100 | 87 | I-approx. 1% |

G — Guanidine Carbonate
AG — aminoguanidine Bicarbonate
G.HCl — Guanidine hydrochloride
AG.HCl — Aminoguanidine Hydrochloride
I — N—Methyl-N—Phosphonomethylglycine
*No Methylaminomethyl phosphoric acid coproduct is found.

EXAMPLE 2

General procedure for separating of NPMG acid and reuse of iminourea salt to reproduce NPMIDA Iminourea salt.

A. A solution of NPMG-Iminourea salt obtained from example I and an equivalent amount of concentrated hydrochloric acid was agitated in the reactor (the final pH is approx. 1.5). The solution was heated up to 100°–105° C. and the formaldehyde co-product was distilled out. After most of the formaldehyde was liberated, the solution was subjected to evaporation under reduced pressure at 60° C. to obtain concentrated solution (25% NPMG in water). After cooling the solution to about 5° C., the NPMG is precipitated as a white solid. The slurry is filtered and the filtrate containing the Iminourea-hydrochloride salt is taken for reuse.

The NPMG acid was analyzed through NMR (see result in table 1).

B. A mixture of NPMIDA (0.52 mole), 600 parts of water and Sodium Hydroxide solution (0.52 mole) was agitated in a suitable reaction vessel at 20° C. After disolution was completed, an equivalent amount of the above Iminourea-Hydrochloride filtrate was slowly added. After stirring for ½ hour, during which part of the NPMIDA-Iminourea was separated, sodium chloride was added to saturate the solution. The insoluble NPMIDA-Imino urea salt is filtered and was analyzed through NMR.

Following the above procedure NPMG and NPMIDA-Iminourea were produced from the following NPMG-Iminourea salt obtained in example 1:

Guanidine, aminoguanidine, di-phenyl guanidine, di-O-tolyl guanidine and methyl guanidine.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come with the meaning and range of equivalency of the claims are therefore intended to be embraced therein.

What is claimed is:

1. A process for producing N-phosphonomethylglycine acid (NPMG) comprising (a) oxidizing an N-(phosphonomethyl) iminodiacetic acid (NPMIDA) derivative of the general formula I

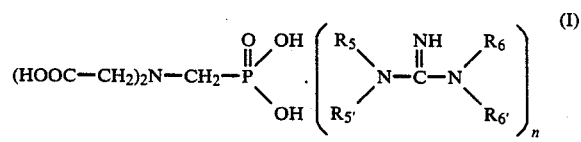

wherein n is 1 or 2 and $R_5$, $R_{5'}$, $R_6$ and $R_{6'}$ are independently H, $NH_2$,

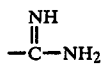

or an aryl, cycloalkyl or straight or branched chain alkyl or alkenyl group optionally substituted by hydroxy or halogen, or an alkylaryl group, provided that at least one of $R_5$, $R_5'$, $R_6$ or $R_6'$ is hydrogen, to produce a corresponding iminourea salt of NPMG and then (b) reacting said salt with an acid stronger than NPMG whereby NPMG is produced and there remains in solution the iminourea salt of said stronger acid.

2. The process of claim 1 comprising adding iminourea strong-acid salts to the solution of the NPMIDA derivatives of the general formula I before the oxidation thereof.

3. The process of claim 2 wherein said strong acid is an inorganic acid selected from the group consisting of hydrochloric acid and sulfuric acid.

4. The process of claim 1 comprising the recycling step of (c) reacting said resulting iminourea salt of said stronger acid with an NPMIDA alkali metal salt to produce a salt of formula I for use in process step (a).

5. A process for producing N-phosphonomethylglycine acid (NPMG) according to claim 1 wherein said acid is an inorganic acid selected from the group consisting of hydrochloric and sulfuric acid.

6. A process for producing N-phosphonomethylglycine acid (NPMG) according to claim 1 wherein the iminourea of said salt of formula I is selected from the group consisting of guanidine, aminoguanidine, diphenylguanidine and di-o-tolyl guanidine.

7. A process for producing N-phosphonomethylglycine acid (NPMG) according to claim 6 wherein said iminourea is guanidine.

8. A process for producing N-phosphonomethylglycine acid (NPMG) according to claim 6 wherein said iminourea is aminoguanidine.

9. A process for producing N-phosphonomethylglycine acid (NPMG) according to claim 4 wherein said alkali metal is selected from the group consisting of sodium and potassium.

10. A process for producing N-phosphonomethylglycine acid (NPMG) according to claim 1 wherein said aryl group is phenyl optionally substituted by one or more halogen or alkyl groups.

11. A process for producing N-phosphonomethylglycine acid (NPMG) according to claim 1 wherein said oxidation is carried out at a temperature of about 70° to about 120° C.

12. A process for producing N-phosphonomethylglycine acid (NPMG) according to claim 1 wherein said oxidation is carried out using molecular oxygen-containing gas in the presence of a metal or activated carbon catalyst.

* * * * *